United States Patent [19]

Philion

[11] Patent Number: 4,614,830

[45] Date of Patent: Sep. 30, 1986

[54] ESTERIFICATION PROCESS

[75] Inventor: Richard E. Philion, Sand Lake, N.Y.

[73] Assignee: Sterling Drug Inc., New York, N.Y.

[21] Appl. No.: 764,163

[22] Filed: Aug. 9, 1985

[51] Int. Cl.$^4$ ............................................. C07C 69/76
[52] U.S. Cl. ...................................... 560/109; 560/19; 560/45
[58] Field of Search ........................... 560/109, 19, 45

[56] References Cited

U.S. PATENT DOCUMENTS

| | | |
|---|---|---|
| 3,904,671 | 9/1975 | Minatoya et al. ................... 560/109 |
| 4,035,404 | 7/1977 | Bodor et al. ......................... 560/109 |
| 4,105,787 | 8/1978 | Jones et al. ......................... 560/109 |
| 4,138,581 | 2/1979 | Minatoya et al. ................... 560/109 |
| 4,503,256 | 3/1985 | Fourie et al. ....................... 560/109 |

FOREIGN PATENT DOCUMENTS

| | | |
|---|---|---|
| 2015573 | 10/1970 | Fed. Rep. of Germany ...... 560/109 |
| 2042295 | 3/1971 | France ................................. 560/109 |
| 58-134059 | 8/1983 | Japan . |
| 58-134060 | 8/1983 | Japan . |

OTHER PUBLICATIONS

Tullar, B. et al. J. Med. Chem. 19(6) 834–8 1976.
Dooley, D. et al. Eur. J. Pharmacol. 70(2) 213–18 1981.
G. Höfle, W. Steglich and H. Vorbrüggen, Angew. Chem. Int. Ed. Engl. 17, 569–583 (1978).

Primary Examiner—Paul J. Killos
Attorney, Agent, or Firm—Thomas L. Johnson; B. Woodrow Wyatt; Paul E. Dupont

[57] ABSTRACT

An improvement in the process for esterification of 3,4-dihydroxyphenyl N-alkylaminoalkyl ketones with arylcarboxylic acid chlorides which comprises carrying out the esterification in the presence of a catalytic amount of a 4-di-lower-alkylaminopyridine or 4-(1-pyrrolidinyl)pyridine and an acid-acceptor comprising a tertiary amine or sterically-hindered secondary amine.

6 Claims, No Drawings

ESTERIFICATION PROCESS

BACKGROUND OF THE INVENTION (a) Field of the Invention

This invention relates to an improved process for esterification of 3,4-dihydroxyphenyl N-alkylaminoalkyl ketones with arylcarboxylic acid chlorides.

(b) Information Disclosure Statement

Minatoya et al. U.S. Pat. No. 4,138,581 Feb. 6, 1979) discloses amino-ketone compounds of the formula

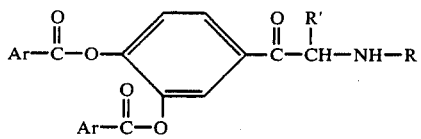

wherein Ar is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms and alkanoylamino having 1-6 carbon atoms; R is alkyl having 1-4 carbon atoms or cycloalkyl having 3-6 carbon atoms; and R' is hydrogen or alkyl of 1-2 carbon atoms. Reduction of said compounds forms the corresponding phenylethanolamines useful as sympathomimetic agents. Said amino-ketones are in turn prepared by esterification of the corresponding diphenolic compounds of the formula

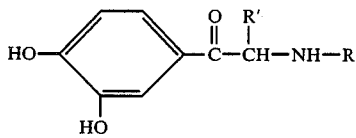

with an acid chloride, Ar-COCl. The esterification is carried out either by reacting an alkali metal salt of the diphenol with the acid chloride, or by heating the hydrochloride salt of the diphenolic compound with the acid chloride in trifluoroacetic acid. Yields of the order of 30-50% are obtained.

The use of 4-dialkylaminopyridines and 4-(1-pyrrolidinyl)pyridine as acylation catalysts is known; cf. G. Höfle, W. Steglich and H. Vorbr/ ggen, Angew. Chem. Int. Ed. Engl. 17, 569–583 (1978). The reference shows the substituted pyridines are effective as catalysts in acylation of both phenols and amines.

SUMMARY OF THE INVENTION

The invention relates to an improvement in the process for preparing an acid-addition salt of a compound of the formula

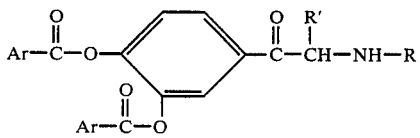

wherein Ar is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms and alkanoylamino having 1-6 carbon atoms; R is alkyl having 1-4 carbon atoms or cycloalkyl having 3-6 carbon atoms; and R' is hydrogen or alkyl of 1-2 carbon atoms, by esterification of the corresponding diphenolic compound of the formula

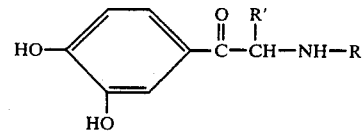

or an acid-addition salt thereof with an acid chloride of the formula ArCOCl; said improvement comprising treating said diphenolic compound in a polar aprotic solvent with at least two molar equivalents of said acid chloride in the presence of a catalytic amount of a 4-di-lower-alkylaminopyridine or 4-(1-pyrrolidinyl)pyridine, and an acid-acceptor comprising a tertiary amine or a sterically-hindered secondary amine present in an amount (a) approximately stoichiometric with respect to the acid chloride when an acid-addition salt of the diphenolic compound is used, or (b) in an amount approximately one-half stoichiometric with respect to the acid chloride when the free base form of the diphenolic compound is used.

DETAILED DESCRIPTION INCLUSIVE OF PREFERRED EMBODIMENTS

The starting materials of Formula II are illustrated by numerous examples in U.S. Pat. No. 4,138,581. A preferred starting material is 3,4-dihydroxyphenyl N-(tert-butyl)aminomethyl ketone [II; $R=C(CH_3)_3$, $R'=H$] or the hydrochloride salt thereof.

A preferred acid chloride is p-toluyl chloride.

The 4-di-lower-alkylaminopyridines used as catalysts are preferably those in which lower-alkyl has 1-2 carbon atoms, thus including 4-dimethylaminopyridine, 4-(methyl)(ethyl)aminopyridine and 4-diethylaminopyridine. A particularly preferred catalyst is 4-dimethylaminopyridine.

The acid-acceptor can be any basic tertiary amine or sterically-hindered secondary amine, the hydrochloride salt of which can readily be separated from the hydrochloride salt of the esterified product. Sterically-hindered amines are those having bulky or branched chain substituents that impede acylation of the amine-nitrogen by the acid chloride. Preferred acid-acceptors are triethylamine, tributylamine and di-isopropylamine. A particularly preferred acid-acceptor is tributylamine.

Illustrative of the polar aprotic solvents which can be used are acetonitrile, acetone, ethyl acetate, isopropyl acetate, dimethylformamide, methylene dichloride and methyl ethyl ketone. Acetonitrile is a preferred solvent.

The reaction is exothermic and the contents warm to from 50° C. to reflux temperature depending upon the rate of addition of the acid chloride. Accordingly, no external heating is necessary.

The catalyst is effective in quantities as low as about 0.01 molar equivalent with respect to the diphenol of Formula II. Larger amounts are of course effective and may serve in the dual role of catalyst and acid-acceptor.

The amount of acid-acceptor to be added to the reaction mixture is that amount needed to take up all of the hydrogen chloride formed in the reaction of the acid chloride with the diphenol. If the hydrochloride or other acid-addition salt of the compound of Formula II is used as the starting material, and the necessary two molar equivalents or a slight excess of acid chloride is employed to esterify both phenol groups, an amount of acid-acceptor approximately stoichiometric with respect to the acid chloride is needed to take up the hydrogen chloride produced in the reaction. On the other hand, if the free base form of the compound of Formula II is used as the starting material, then only half the quantity of acid-acceptor is needed since the substrate base product of Formula I also acts as an acid-acceptor.

In view of the teaching of the prior art that 4-dialkylaminopyridines are useful as catalysts in acylating both phenols and amines, it was surprising to find that in the process of the instant invention acylation of the phenolic groups occurred essentially exclusively. Increased amide formation was observed when non-polar solvents were used.

The improvement of the present invention has a number of distinct advantages over the prior art processes.

The preferred process of the prior art (U.S. Pat. No. 4,138,581) involves reaction of the acid chloride with the diphenolic compound (II) in trifluoroacetic acid solution. Illustrative of the prior art process is Example 111 of said patent wherein nearly 100% excess of acid chloride was used and the product was obtained in 54% yield. The several advantages of the instant process are as follows:

(a) The corrosive and expensive trifluoroacetic acid is replaced by relatively innocuous and inexpensive solvents.
(b) The yields are increased to 60–80%.
(c) The excess acid chloride can be reduced to 5 mole percent.
(d) Material costs are reduced and when completed with improved yields result in more than 50% cost reduction.

The following examples will illustrate the invention without the latter being limited thereby.

EXAMPLE 1

To a stirred mixture of 260 g (1.0 mole) of 3,4-dihydroxyphenyl N-(tert-butyl)aminomethyl ketone [II; R=C(CH$_3$)$_3$, R'=H] as the hydrochloride salt in 2.6 liters of acetonitrile was rapidly added 380 g (2.05 moles) of tributylamine at room temperature. The resulting suspension was stirred for about 20 minutes and 6.7 g (0.055 mole) of 4-dimethylaminopyridine was then added followed by dropwise addition of 325 g (2.10 moles) of p-toluylchloride over a period of 35–40 minutes. At this rate of addition the temperature of the reaction mixture did not exceed 50° C. The reaction mixture was stirred until the temperature decreased to 40° C., and was then cooled with tap water and filtered. The solid product was sucked as dry as possible and rinsed three times with 160 ml portions of acetone or acetonitrile at 5° C. The colorless product was dried overnivght at 50° C. in a drying oven to give 3,4-bis(p-toluyloxy)phenyl N-(tert-butyl)aminomethyl ketone hydrochloride I [Ar=4-CH$_3$C$_6$H$_4$, R=C(CH$_3$)$_3$, R'=H] in crude yields of 78.4–85.5%. When corrected for water and tributylamine hydrochloride content the corrected yields ranged from 74 to 80%. When the filter cake was washed with acetone, less than 1 percent of tributylamine hydrochloride was present. The pure product has the melting point 217°–220° C.

It is contemplated that similar results can be obtained by replacing the 4-dimethylaminopyridine by a molar equivalent amount of 4-(1-pyrrolidinyl)pyridine.

It is further contemplated that similar results can be obtained starting with the free base form of 3,4-dihydroxyphenyl N-(tert-butyl)aminomethyl ketone (224 g, 1.0 mole) and using 190 g (1.025 mole) instead of 380 g of tributylamine.

EXAMPLE 2

The process of Example 1 was repeated substituting the tributylamine by a molar equivalent amount of diisopropylamine. Starting with 26 g of 3,4-dihydroxyphenyl N-(tert-butyl)aminomethyl ketone hydrochloride there was obtained 44.6 g of crude product containing 38.9 g (78% yield) of 3,4-bis(p-toluyloxy)phenyl N-(tert-butyl)aminomethyl ketone hydrochloride, the remainder consisting of tributylamine hydrochloride.

EXAMPLE 3

The process of Example 1 was repeated substituting isopropyl acetate for the acetonitrile as solvent. Starting with 26 g of 3,4-dihydroxyphenyl N-(tert-butyl)aminomethyl ketone hydrochloride there was obtained 34 g of crude product containing 32 g (60% yield) of 3,4-bis-(p-toluyloxy)phenyl N-(tert-butyl)aminomethyl ketone hydrochloride, the remainder consisting of tributylamine hydrochloride.

EXAMPLE 4

The process of Example 1 was repeated substituting acetone for the acetonitrile as solvent. Starting with 26 g of 3,4-dihydroxyphenyl N-(tert-butyl)aminomethyl ketone hydrochloride there was obtained 33 g of 3,4-bis-(p-toluyloxy)phenyl N-(tert-butyl)aminomethyl ketone hydrochloride (64% yield) containing only a trace of tributylamine hydrochloride.

EXAMPLE 5

The process of Example 1 was repeated substituting the tributylamine by a molar equivalent amount of triethylamine. In this instance the oven-dried crude product was diluted with about 2 volumes of distilled water, heated on a steam bath to 45°–50° C. and filtered. The filter cake was rinsed with water and isopropyl acetate. From 260 g of 3,4-dihydroxyphenyl N-(tert-butyl)aminomethyl ketone hydrochloride there was obtained 470 g of product containing 360 g (73% yield) of 3,4-bis(p-toluyloxy)-phenyl N-(tert-butyl)aminomethyl ketone hydrochloride, the remainder consisting of water and triethylamine hydrochloride.

EXAMPLE 6

The process of Example 1 was repeated substituting the tributylamine by a molar equivalent amount of triethylamine, and substituting acetonitrile by acetone as the solvent. The crude product was treated with water as in Example 5. From 26 g of 3,4-dihydroxyphenyl N-(tert-butyl)aminomethyl ketone hydrochloride there was obtained 46.5 of product containing 31.8 g (64% yield) of 3,4-bis(p-toluyloxy)phenyl N-(tert-butyl)aminomethyl ketone hydrochloride, 22% of the remainder comprising triethylamine hydrochloride.

EXAMPLE 7

To a stirred suspension of 26.0 g (0.10 mole) of 3,4-dihydroxyphenyl N-(tert-butyl)aminomethyl ketone hydrochloride in 260 ml of acetonitrile was added 38.7 g (0.209 mole) of tributylamine, followed after 10 minutes by 600 mg of 4-(1-pyrrolidinyl)pyridine. To this mixture was added 33 g (0.213 mole) of p-toluyl chloride dropwise over a 20 minute period. The reaction mixture was allowed to stand at room temperature and the crystalline product which separated was collected by filtration and dried to give 33 g (66% yield) of 3,4-bis(p-toluyloxy)phenyl N-(tert-butyl)aminomethyl ketone hydrochloride, indicated to be essentially pure by thin layer chromatography.

EXAMPLE 8

To a stirred suspension of 13.0 g (0.059 mole) of 3,4-dihydroxyphenyl N-(tert-butyl)aminomethyl ketone [free base form, m.p. 175° C.(decompn), prepd. from the hydrochloride salt and tributylamine in acetone solution] in 130 ml of acetonitrile was added 9.4 g (0.05 mole) of tributylamine and 400 mg of 4-dimethylaminopyridine. The mixture was stirred for 10 minutes and then 16 g (0.103 mole) of p-toluyl chloride was added dropwise. The reaction mixture was stirred for one hour, and the solid product which separated was collected by filtration to give 19.3 g (67%) of 3,4-bis(p-toluyloxy)phenyl N-(tert-butyl)aminomethyl ketone hydrochloride.

The crude products of the foregoing examples containing minor amounts of acid-acceptor amine hydrochloride can be used without further purification in the reduction step to produce the corresponding phenylethanolamine compound. For example, a sample of 3,4-bis(p-toluyloxy)phenyl N-(tert-butyl)aminomethyl ketone hydrochloride containing about 6 percent of tributylamine hydrochloride was reduced with sodium borohydride to give 3,4-bis(p-toluyloxy)-α-[(tert-butylamino)methyl]benzyl alcohol (bitolterol) in greater than 90% yield.

I claim:

1. In the process for preparing an acid-addition salt of a compound of the formula

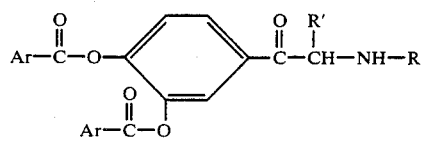

wherein Ar is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms and alkanoylamino having 1-6 carbon atoms; R is alkyl having 1-4 carbon atoms or cycloalkyl having 3-6 carbon atoms; and R' is hydrogen or alkyl of 1-2 carbon atoms, by esterification of the corresponding diphenolic compound of the formula

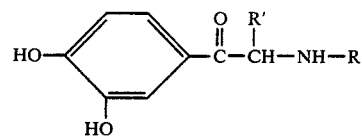

or an acid-addition salt thereof with an acid chloride of the formula ArCOCl;

the improvement which comprises treating said diphenolic compound in a polar aprotic solvent with at least two molar equivalents of said acid chloride in the presence of a catalytic amount of a 4-di-lower-alkylaminopyridine or 4-(1-pyrrolidinyl)pyridine, and an acid-acceptor comprising a tertiary amine or sterically-hindered secondary amine present in an amount (a) approximately stoichiometric with respect to the acid chloride when an acid-addition salt of the diphenolic compound is used; or (b) in an amount approximately one-half stoichiometric with respect to the acid chloride when the free base form of the diphenolic compound is used.

2. The process according to claim 1 wherein said diphenolic compound is 3,4-dihydroxyphenyl N-(tert-butyl)aminomethyl ketone or the hydrochloride salt thereof, and the acid chloride is p-toluyl chloride.

3. The process according to claim 2 wherein the acid-acceptor is tributylamine.

4. The process according to claim 2 wherein the polar aprotic solvent is acetonitrile.

5. The process according to claim 2 wherein the catalyst is 4-dimethylaminopyridine.

6. The process according to claim 2 wherein the catalyst is 4-(1-pyrrolidinyl)pyridine.

* * * * *